US00PP33265P2

(12) United States Plant Patent
Hansen

(10) Patent No.: US PP33,265 P2
(45) Date of Patent: Jul. 13, 2021

(54) ***HOSTA* PLANT NAMED 'VOICES IN THE WIND'**

(50) Latin Name: ***Hosta* hybrid (Tratt.)**
Varietal Denomination: Voices in the Wind

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,296

(22) Filed: Dec. 18, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

(56) References Cited

PUBLICATIONS http://www.plantsgalore.com/hostas/cultivars/V/Hosta_Voices_in_the_Wind.htm Retrieved from the Internet on Mar. 30, 2021. (3 pages total).*

* cited by examiner

*Primary Examiner* — Susan McCormick Ewoldt

(57) ABSTRACT

A new and distinct *Hosta* plant named 'Voices in the Wind' of medium-sized, arching, long, lanceolate, bluish-green leaves having wavy creamy-yellow margins with numerous feathering intermediate colors and a narrowly acute curling apex. The flowers are pale lavender with darker lavender veins appearing in mid-July. Prior to flower bud opening, the floral bracts produce a broad, short, light lavender, water-lily effect of compact lanceolate bracts. 'Voices in the Wind' is attractive and is useful in the landscape, as a specimen or en masse or as a container plant.

2 Drawing Sheets

Botanical classification: *Hosta* hybrid (Tratt.).
Variety denomination: 'Voices in the Wind'.

STATEMENT REGARDING PRIOR DISCLOSURES UNDER 37 CFR 1.77(B)(6)

*Hosta* 'Voices in the Wind' was first introduced by the inventor as a non-enabling description through The American *Hosta* Society which is the International Cultivar Registration Authority registration in early 2020. No plants of *Hosta* 'Voices in the Wind' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Voices in the Wind' hereinafter also referred to as the new plant or by the cultivar name, 'Voices in the Wind'. *Hosta* 'Voices in the Wind' was a cross by the inventor between two non-patented, unreleased, proprietary hybrids on Jul. 22, 2013 at a wholesale perennial nursery in Zeeland, Mich., USA. The female parent was identified as a proprietary, unreleased sport known only as "streaked 'Arctic Blast'" (not patented) and the male parent was the proprietary, unreleased, unnamed hybrid known only as 'H10-162' (not patented). The new plant was assigned the breeder code 13-332-1 and passed the initial evaluation in the summer of 2014. It has been asexually propagated by division at the same nursery since 2017 and also by careful shoot tip plant tissue culture with the resultant asexually propagated plants having retained all the same traits as the original plant. *Hosta* 'Voices in the Wind' is stable and reproduces true to type in successive generations of asexual reproduction.

There are nearly 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are 'Drop-dead Gorgeous' U.S. Plant patent application Ser. No. 16/974,101, 'Joy Ride' (not patented), 'Hope Springs Eternal' copending U.S. Plant patent application Ser. No. 16/974,300, 'Landslide' (not patented), 'Chantilly Lace' (not patented), 'Greybeard' (not patented), 'Tears in Heaven' copending U.S. Plant patent application Ser. No. 16/974,298 and 'Neptune' U.S. Plant Pat. No. 19,674.

'Drop-dead Gorgeous' has similar wavy margins, but the center is not as glaucous bluish-green and the variegation is more yellowish. 'Joy Ride' has a flatter habit and does not have variegated foliage, the leaf blades are more pointed and the margin is not as wavy. 'Hope Springs Eternal' is similar in size but flatter and less upright in habit with a more cordate foliage and less pointed and curled leaf tip. 'Landslide' has a flatter habit and the margin variegation is not as wide nor as wavy as the new plant. 'Chantilly Lace' has a smaller habit and foliage and the leaves are not elongated nor as wavy. 'Greybeard' has slightly larger habit and leaf size, but the leaves are more cordate, the margin is thinner and less wavy, and the center is less glaucous bluish-green. 'Tears in Heaven' has solid glaucous foliage without variegation that is more cupped. 'Neptune' has solid blue-green leaf without variegation and the leaves are broader and the margin is not as wavy.

The female parent has leaves with random streaked variegation in the margin and center without ruffled leaf margins but the foliage is not as elongated or as glaucous. The male parent has larger leaves and slightly larger habit with intensely glaucous leaves that are not variegated.

Other *Hosta* cultivars may have ovate leaf blades with yellow variegated margins and blue-green centers, thick leaf substance or other individual traits similar to 'Voices in the Wind' but the new plant differs from the above listed cultivars and all other *Hostas* known to the applicant, by the combination of the following traits.

1. Leaves are medium-sized, long, lanceolate, with broadly acute apices and cordate base;
2. Arching leaves have an intensely-wavy creamy-yellow margin and a narrowly acute curling apex;
3. Leaf center is bluish-green with numerous featherings of intermediate colors between the margin and center;
4. Flowers are pale lavender beginning in mid-July;
5. Floral bracts form broad, short, light-lavender, water-lily effect well before flowers buds open;
6. Medium mounded habit and useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show a six-year-old 'Voices in the Wind' plant in a trial garden at a nursery in Zeeland, Mich. with supplement fertilizer and water as needed.

DETAILED BOTANICAL DESCRIPTION

Figure 1:
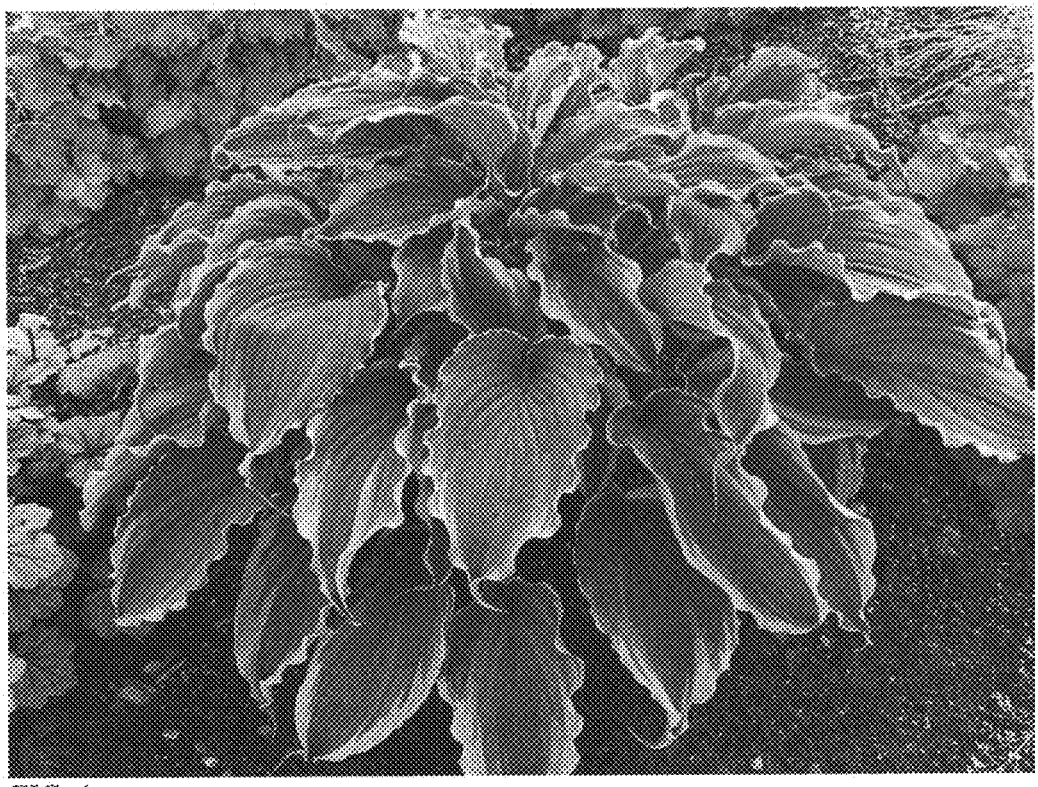
FIG. 1 shows the landscape foliage habit of a new plant just before flowering.
Figure 2:
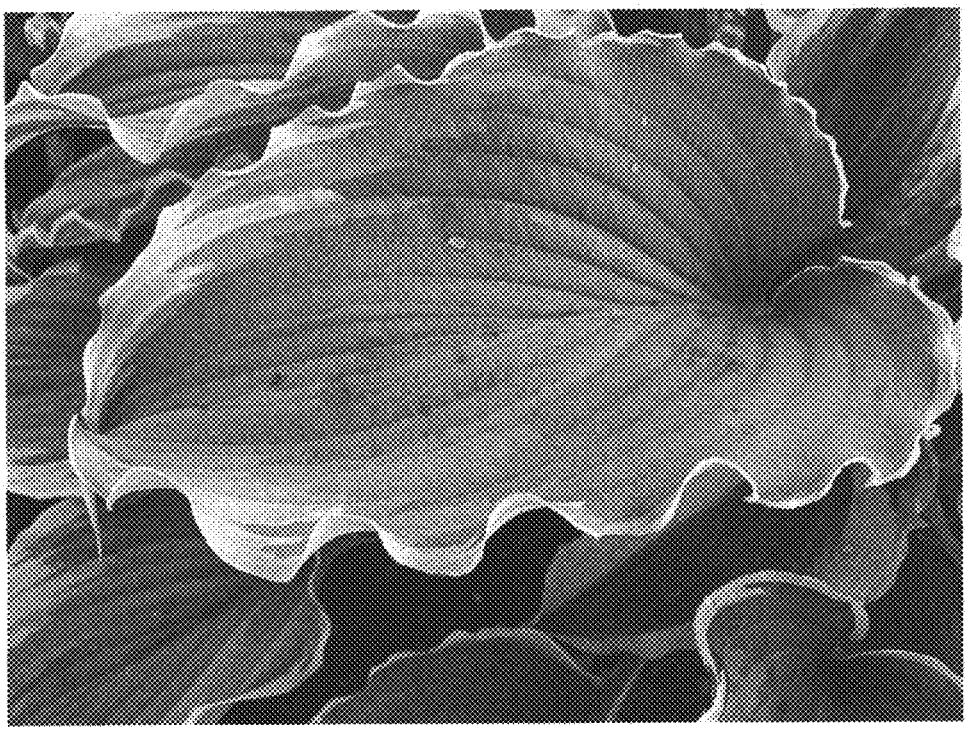
FIG. 2 shows a close-up of the flowers and buds.
Figure 3:
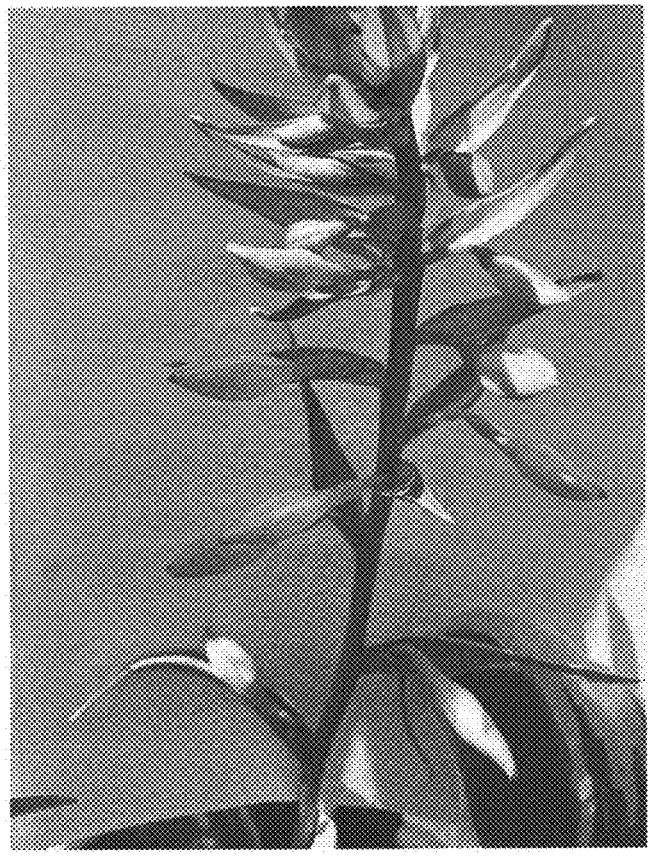
FIG. 3 shows a close-up of the foliage.
Figure 4:
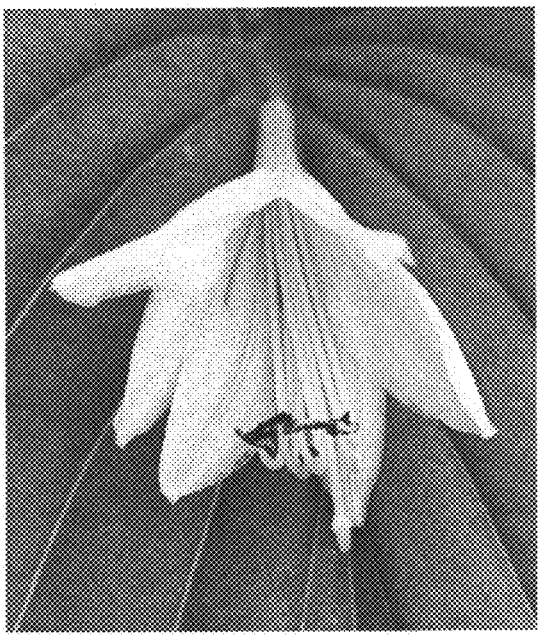
FIG. 4 shows a close-up of the inside of a single flower.

The following descriptions and color references are based on the 2015 edition of The Royal Horticultural Society Colour Chart except where common dictionary terms are used. The new plant, *Hosta* 'Voices in the Wind', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Mich. with supplemental water and fertilizer.

Botanical classification: *Hosta* x hybrid;

Parentage: Female or seed parent the proprietary "streaked 'Arctic Blast'"; male or pollen parent 'H10-162' comprising of 'Neptune', 'Winfield Blue' (not patented) and 'Joy Ride' (not patented);

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a large mound of arching petioles and leaves and erect scapes flowering above foliage;

Plant size: Foliage height to about 43.2 cm above soil line to the top of the leaves, to about 73.7 cm tall to the top of the flowers and to about 116.8 cm wide at the widest point at the soil line;

Foliage description: Lanceolate; narrowly-acute curving apex, cordate base; margin entire, heavily sinuate; glabrous and matte both adaxial and abaxial; flexible but stiff; smooth, not bullate; shallowly impressed adaxial veins and costate abaxial veins;

Leaf blade size: To about 30.5 cm long and about 15.2 cm wide; average about 28.5 cm long and 14.0 cm wide; margin to about 3.8 cm wide;

Leaf blade color: Early season and expanding adaxial margin between RHS 150C and RHS 150D. abaxial margin nearest between HRS 145C and RHS 150D, adaxial center nearest RHS 137A and abaxial center nearest RHS 137C, adaxial intermediate colors comprising RHS 138B, RHS 147C and between RHS 145C and RHS 146D, abaxial intermediate colors comprising RHA 146C and between RHS N138D and RHS 194C; mid-season and mature adaxial margins nearest RHS 150D, abaxial margin nearest RHS 150D, adaxial center RHS 137A, abaxial center nearest RHS N138C, adaxial intermediate colors comprising RHS 148D, RHS 145C, between RHS 148D and RHS N138D and between RHS145D and RHS 148D, abaxial intermediate colors comprising RHS 147C, RHS 146D and between RHS 145C and RHS 146D;

Petiole: Glabrous and slightly glaucous both adaxial and abaxial; deeply concavo-convex proximally and more shallowly concavo-convex distally; stiff; to 27.5 cm long and 12.0 mm wide at base and about 8.0 mm deep near base, average about 26.0 cm long and 10.0 mm wide;

Petiole color: Adaxial nearest RHS 138A, margins about 1.0 mm wide nearest RHS 150D; abaxial center nearest RHS 138B, margins about 1.0 mm wide nearest RHS 150D;

Veins: Ten to twelve pairs and midrib; parallel; lightly impressed adaxial; costate and smooth abaxial;

Veins color: Young and mature adaxial nearest RHS 157A, abaxial between RHS 147C and RHS 147B;

Flower description:

Buds one to two days prior to opening: Clavate with rounded apex and narrow tube base; about 45.0 mm long and 10.0 mm in diameter at widest with base narrowing in basal 14.0 mm to about 3.5 mm diameter;

Bud color: Bulb between RHS 85D and RHS NN155D and tube nearest RHS 85D;

Flowers: Perfect; flared campanulate; outwardly; to 50.0 mm long to exserted stigma; corolla fused in basal 27.0 mm, free in the distal 20.0 mm, about 46.0 mm long and 36.0 mm wide at tepal apices, decreasing distally; corolla tube portion 15.0 mm long and 3.5 mm diameter; persists for a normal period, usually about one day on plant; flowers tightly arranged on scape;

Flowering period: Scapes remain effective with flowers beginning mid-July for about three and a half weeks; with about 40 flowers per scape; mostly secund;

Fragrance: No detectable fragrance;

Tepal: Two nearly identical sets of three, glabrous; entire margins;

*Inner set*.—About 47.0 mm long and 10.0 mm wide slightly above fusion point; fused in basal 27.0 mm; clavate with broadly acute apex; margin entire with irregular blotchy 1.0 mm wide transparent border; basal 20.0 mm fused into tube.

*Inner set color*.—Vitreous in blotchy irregular pattern along distal margin; adaxial 2.5 mm wide center from base (including corolla tube) to apex between RHS 85C and RHS 85D and margin nearest RHS NN155D, abaxial center lighter than RHS 85D, corolla tube portion nearest RHS 85C and distal margins nearest RHS NN155D.

*Outer set*.—About 47.0 mm long and 9.0 mm wide slightly above fusion point; fused in basal 27.0 mm; clavate with broadly acute apex; entire margin without transparent border; base fused into tube.

*Outer set color*.—Adaxial center distally between RHS 85D and RHS NN155D with corolla tube portion nearest RHS 85C and 1.0 mm margin nearest RHS NN155D with center veins nearest RHS 85C; abaxial corolla tube nearest RHS 85D and distally between RHS 85D and RHS NN155D fading toward margin to nearest RHS NN155D in outer 2.0 mm without obvious veins.

Gynoecium: Single; 54.0 mm long; superior;

*Style*.—Cylindrical; about 46.0 mm long, 1.0 mm diameter; curved upward 90 degrees in distal 5.0 mm; color nearest RHS 145D proximally and nearest RHS 157D distally.

*Stigma*.—Puberulent; tri-lobed; about 1.2 mm across and 1.0 mm tall; color nearest RHS 157C.

*Ovary*.—Ellipsoidal; superior; apex rounded; base rounded to truncate; longitudinally sulcate; to about 7.0 mm long and 2.5 mm diameter in middle; color nearest RHS 145A.

Androecium: Six;

*Filaments*.—Six, approximately 50.0 mm long and 1.0 mm in diameter; curved upward to nearly 90 degrees in the distal 5.0 mm; color distally nearest RHS 155C, base nearest RHS 145D.

*Anthers*.—Ellipsoidal with rounded ends; dorsifixed, longitudinally dehiscent; about 4.5 mm long and 1.5 mm wide; color prior to dehiscing nearest RHS N187 adaxial and abaxial.

*Pollen*.—Spherical; less than 0.1 mm long; color nearest RHS 13B.

Flower fragrance: None observed;

Peduncle: Cylindrical; usually one per mature division; about 4 per plant; glabrous, slightly glaucous; erect; to about 73.7 cm tall, and about 9.0 mm in diameter at base, average about 68.0 cm tall and 8.0 mm diameter at base;

Inflorescence: Flowering portion about 25.0 cm long and 7.0 cm wide; with pale lavender flowers and large floral bracts subtending each flower;

Peduncle color: Proximal portion below leaves nearest RHS 138B and distal portion nearest RHS 138A;

Pedicel: Variable in length; terete; glabrous; slightly lustrous; about 11.0 mm to 14.0 mm long and 2.0 mm diameter; outwardly to slightly drooping;

Pedicel color: Variable; nearest RHS 138B;

Floral bracts: Each flower normally subtended by a single bract; lanceolate to linear; narrowly acute apex and truncate clasping base; entire margin; glabrous and glaucous lustrous abaxial and adaxial; to about 9.0 cm long 1.1 cm wide, decreasing distally; prior to flower development forming compact attractive cluster about 12 cm across; persisting while flowers open;

Bract color: Distal adaxial and abaxial between RHS 146D and RHS 145B with strong longitudinal blushing of RHS 79D, with narrow margins nearest RHS NN155B;

Fruit: Tri-valved dehiscent capsule; ellipsoidal to cylindrical with apex apiculate to acute and attenuate base; about 25.0 mm long and 8.0 mm diameter;

Fruit color: Nearest RHS 138B as maturing and RHS 161D when ripe;

Seed: Typically about 15 per capsule; endospermic; flattened-ellipsoidal wing surrounding embryo at one end of ellipse; to about 7.0 mm long, 3.0 mm wide and 1.5 mm thick at embryo;

Seed color: Nearest RHS 202A;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth conditions: The plant grows best and shows best coloration with plenty of moisture, adequate drainage and light shade, but is able to tolerate some drought when mature. Hardiness at least from USDA zone 3 through 8, and other disease resistance is typical of that of other *Hostas*.

It is claimed:

1. A new and distinct *Hosta* plant cultivar named *Hosta* 'Voices in the Wind' as herein described and illustrated.

* * * * *